(12) United States Patent
Golden

(10) Patent No.: US 9,655,689 B2
(45) Date of Patent: May 23, 2017

(54) FORCEPS FOR MOLAR EXTRACTION

(75) Inventor: Richard Golden, Detroit, MI (US)

(73) Assignee: Beak and Bumper, LLC, Detroit, MI (US)

( * ) Notice: Subject to any disclaimer, the term of this patent is extended or adjusted under 35 U.S.C. 154(b) by 756 days.

(21) Appl. No.: 12/789,732

(22) Filed: May 28, 2010

(65) Prior Publication Data

US 2010/0240008 A1    Sep. 23, 2010

Related U.S. Application Data

(63) Continuation of application No. 11/095,355, filed on Mar. 31, 2005.

(60) Provisional application No. 61/268,523, filed on Jun. 12, 2009.

(51) Int. Cl.
*A61C 3/14*    (2006.01)

(52) U.S. Cl.
CPC ..................... *A61C 3/14* (2013.01)

(58) Field of Classification Search
CPC ....................................... A61C 3/14
USPC ......... 433/3–4, 159; 81/415–416, 418, 424.5
See application file for complete search history.

(56) References Cited

U.S. PATENT DOCUMENTS

| 4,261 A | 11/1845 | Baker et al. |
|---|---|---|
| 8,351 A | 9/1851 | Burch |
| 75,716 A | 3/1868 | Woolverton |
| 97,399 A | 11/1869 | Holmes |
| 145,058 A | 12/1873 | French |
| 354,863 A | 12/1886 | Hughes |
| 390,561 A | 10/1888 | Brown |
| 478,217 A | 7/1892 | Blake, Sr. |
| 491,519 A | 2/1893 | Blake, Sr. |
| 491,932 A | 2/1893 | Whitlock |
| 536,166 A | 3/1895 | Angle |
| 553,718 A | 1/1896 | Monfort |

(Continued)

FOREIGN PATENT DOCUMENTS

| CA | 2492576 A1 | 7/2006 |
|---|---|---|
| KR | 200270833 Y1 | 4/2002 |

(Continued)

OTHER PUBLICATIONS

Bennion, Antique Dental Instruments, 1986, Chapter 2, pp. 29-38, Sotheby's Publications, London.

(Continued)

*Primary Examiner* — Cris L Rodriguez
*Assistant Examiner* — Hao D Mai
(74) *Attorney, Agent, or Firm* — Dinsmore & Shohl LLP; Douglas Mcevoy

(57) ABSTRACT

A dental forceps for removal of rear molars having first and second handles which are pivotally connected. Forward distal ends of the handles terminate, respectively, in a first handle support with an end most pad exhibiting a three dimensional and rounded surface profile extending laterally to one side, as well as a second handle terminating in a correspondingly angled beak. The arrangement of the pad and beak are such that, upon setting in position at the desired molar by placing the rounded and width extending pad support upon the gum of the patient between the molar and the cheek and concurrently placing the pointed beak on the lingual side of the molar, an outward rotating force is then exerted on the handles to roll (or rotate) the pad and beak such that the molar is forcibly extracted.

5 Claims, 8 Drawing Sheets

(56) References Cited

U.S. PATENT DOCUMENTS

| | | |
|---|---|---|
| 610,840 A | 9/1898 | Angle |
| 617,587 A | 1/1899 | Link |
| 681,224 A | 8/1901 | Jacob |
| 732,288 A | 6/1903 | Felsch |
| 831,307 A | 9/1906 | Spahn |
| 833,375 A | 10/1906 | Dollar |
| 882,404 A | 3/1908 | Miner |
| 902,570 A | 11/1908 | Ellis |
| 908,056 A | 12/1908 | Whitney et al. |
| 996,030 A | 6/1911 | Parker |
| 1,276,274 A | 8/1918 | Shaffer |
| 1,395,714 A | 11/1921 | Johnson |
| 1,399,265 A | 12/1921 | Lay |
| 1,626,226 A | 4/1927 | Cantor |
| 1,628,499 A | 5/1927 | Joesch |
| 1,674,485 A | 6/1928 | Smith |
| 1,675,815 A | 7/1928 | Miller |
| 1,678,313 A | 7/1928 | Atkinson |
| 1,782,364 A | 11/1930 | Nation |
| 1,866,771 A | 7/1932 | Johnson |
| 2,030,798 A | 2/1936 | Krajeski |
| 2,212,801 A | 8/1940 | Torbert |
| D145,058 S | 6/1946 | French |
| 2,428,689 A | 10/1947 | Sykes |
| 2,430,271 A | 11/1947 | Brantley |
| 2,497,254 A | 2/1950 | Brantley |
| 2,504,227 A | 4/1950 | Rubba |
| 2,507,784 A | 5/1950 | Hamel |
| 2,563,920 A | 8/1951 | Christensen |
| 2,592,641 A | 4/1952 | Balderstone |
| 2,698,483 A | 1/1955 | Berkowitz |
| 2,944,341 A | 7/1960 | Lane |
| 3,456,349 A | 7/1969 | Heimann |
| 3,468,031 A | 9/1969 | Mumaw |
| 3,644,998 A | 2/1972 | Rubino |
| 3,685,097 A | 8/1972 | Scott et al. |
| 3,834,026 A | 9/1974 | Klein |
| 3,866,324 A | 2/1975 | Walser |
| 3,898,738 A | 8/1975 | Linder |
| 4,014,226 A | 3/1977 | Karamarkovich |
| 4,028,969 A | 6/1977 | Politte |
| 4,031,624 A | 6/1977 | Heimann |
| RE29,889 E | 1/1979 | Klein |
| D253,088 S | 10/1979 | Levin |
| 4,230,454 A | 10/1980 | Lococo et al. |
| 4,443,196 A | 4/1984 | Rico |
| 4,559,853 A | 12/1985 | Oye |
| 4,609,353 A | 9/1986 | Kline |
| D296,822 S | 7/1988 | Fenton |
| 5,044,954 A | 9/1991 | Lukase et al. |
| 5,057,016 A | 10/1991 | Lukase et al. |
| 5,122,058 A | 6/1992 | Lukase et al. |
| 5,205,734 A | 4/1993 | Marangoni et al. |
| D335,249 S | 5/1993 | Hopkins |
| 5,368,600 A | 11/1994 | Failla et al. |
| D362,293 S | 9/1995 | Formaggioni |
| D370,161 S | 5/1996 | Snyder |
| 5,538,421 A | 7/1996 | Aspel |
| D392,167 S | 3/1998 | Cockrell et al. |
| 5,735,857 A | 4/1998 | Lane |
| 5,755,573 A | 5/1998 | LeBlanc |
| D396,619 S | 8/1998 | Hunter |
| 5,833,460 A | 11/1998 | Maeda |
| 5,996,450 A | 12/1999 | St. John |
| 6,042,379 A | 3/2000 | Rodriguez del Val |
| D426,440 S | 6/2000 | Torres |
| 6,210,161 B1 | 4/2001 | Montgomery |
| 6,280,184 B1 | 8/2001 | Hamilton |
| 6,293,790 B1 | 9/2001 | Hilliard |
| 6,345,983 B1 | 2/2002 | Godfrey |
| 6,579,296 B1 | 6/2003 | Macey |
| D490,288 S | 5/2004 | Griffin |
| 6,745,648 B2 | 6/2004 | Stier |
| 6,790,037 B1 | 9/2004 | Orecchia |
| 6,910,890 B2 | 6/2005 | Golden |
| 6,934,991 B2 | 8/2005 | Kinkade |
| 7,021,932 B2 | 4/2006 | Standish |
| 7,128,575 B1 | 10/2006 | Sohn |
| D543,813 S | 6/2007 | Tutorow |
| D561,899 S | 2/2008 | Golden |
| 7,344,375 B2 | 3/2008 | Mukasa et al. |
| D566,840 S | 4/2008 | Golden |
| D567,376 S | 4/2008 | Golden |
| 2002/0146665 A1 | 10/2002 | Tamura |
| 2004/0101805 A1 | 5/2004 | Golden |
| 2004/0152044 A1 | 8/2004 | Khan-Sullman |
| 2004/0159194 A1 | 8/2004 | Ting |
| 2005/0070955 A1 | 3/2005 | Young |
| 2005/0170314 A1 | 8/2005 | Golden |
| 2005/0186536 A1 | 8/2005 | Zepf |
| 2005/0214719 A1 | 9/2005 | Hermann |
| 2006/0166167 A1 | 7/2006 | Syfrig |
| 2008/0187885 A1 | 8/2008 | Golden |
| 2008/0254410 A1 | 10/2008 | Golden |

FOREIGN PATENT DOCUMENTS

| | | |
|---|---|---|
| WO | WO-2008097954 A1 | 8/2008 |
| WO | WO-2008097961 A1 | 8/2008 |

OTHER PUBLICATIONS

Harris, The Principles and Practice of Dental Surgery, Eight Edition, pp. 361-363, 1863, Lindsay & Blakiston, Philadelphia.

Ring, Dentistry—An Illustrated History, Sep. 1985, Abradale Press and Harry N. Abrams, Inc.

Coombs, Eagle Beak molar forceps: evolution and usage, Australian Dental Journal, 1985, pp. 360-363, vol. 30, No. 5.

Instrument Darwinism, Sally Dummer traces the evolution of an extraction tool, BDANews, May 2008, p. 22, vol. 21, No. 5.

"A Pictorial History of Dentistry" from http://www.dentalassistant.net/pictorial-history/. (Believed to have been offered for sale, publicly used, and/or published prior to the filed of this application.)

Atkinson, Some early dental extraction instruments including the pelican, bird or axe?, Australian Dental Journal, 2002, pp. 90-93, vol. 47, No. 2, pp. 90-93.

Hyson, The Dental Key: A Dangerous and Barbarous Instrument, Journal of the History of Dentistry, Nov. 2005, pp. 95-96, vol. 53, No. 3.

Wynbrandt, The Excruciating History of Dentistry: Toothsome Tales & Oral Oddities from Babylon to Braces, 1998, pp. 70-71, St. Martin's Press, New York.

Fillebrown, The Use of the Key, The Dental Cosmos, Feb. 1885, pp. 69-74, vol. 27, No. 2.

Busch, Tooth Keys, Journal of the History of Dentistry, Jul. 2003, pp. 57-59, vol. 51, No. 2.

Harn et al., Unusual Instrument Relationship—Wrench or Turnkey, Journal of the History of Dentistry, Mar. 1996, pp. 25-26, vol. 44 No. 1.

Baker & Riley, Lever operated Toothkey, patented 1845, obtained from "http://dmd.co.il/antiques/big_he.html".

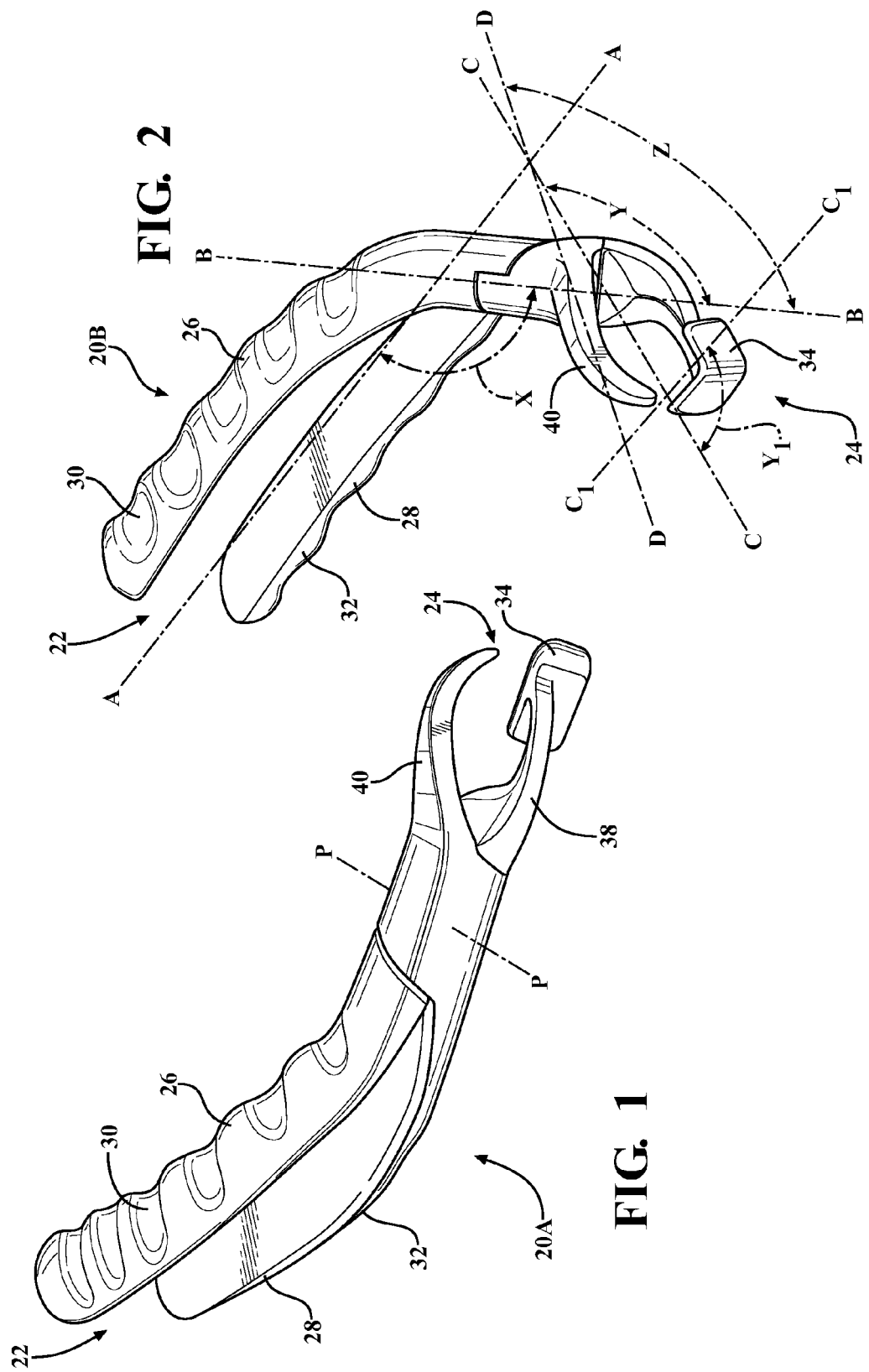

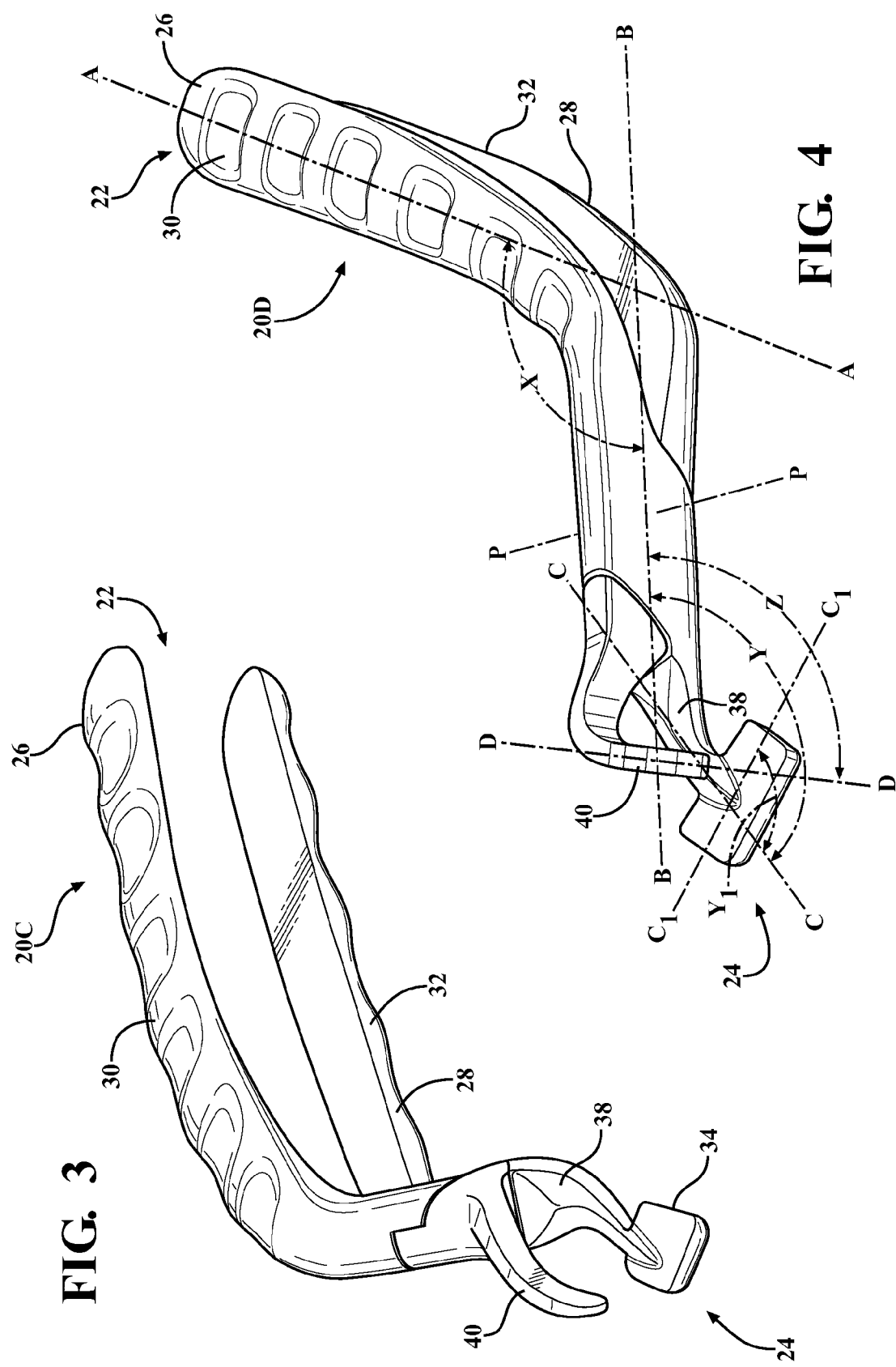

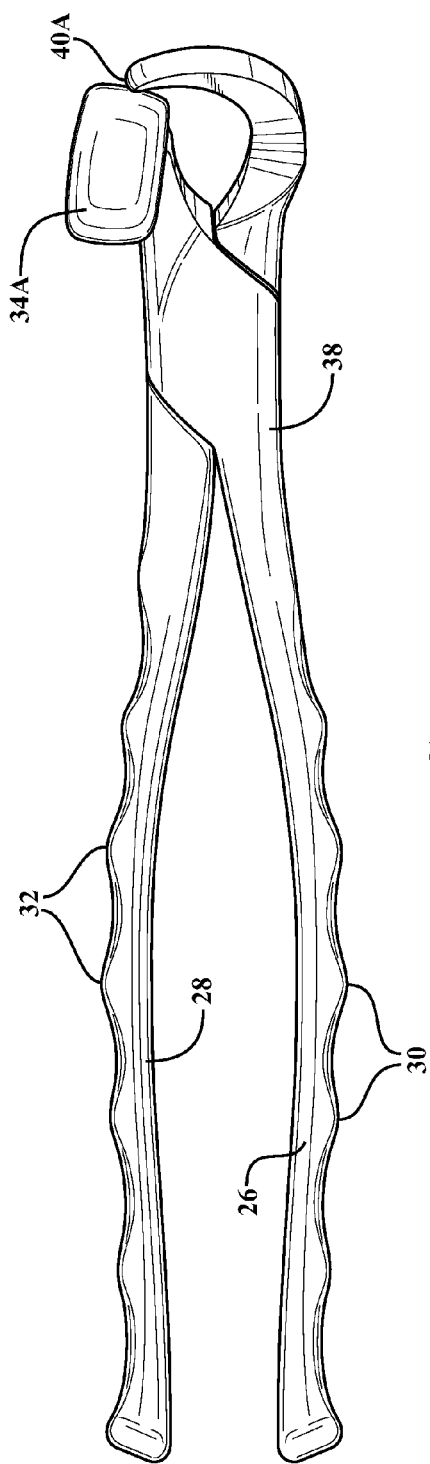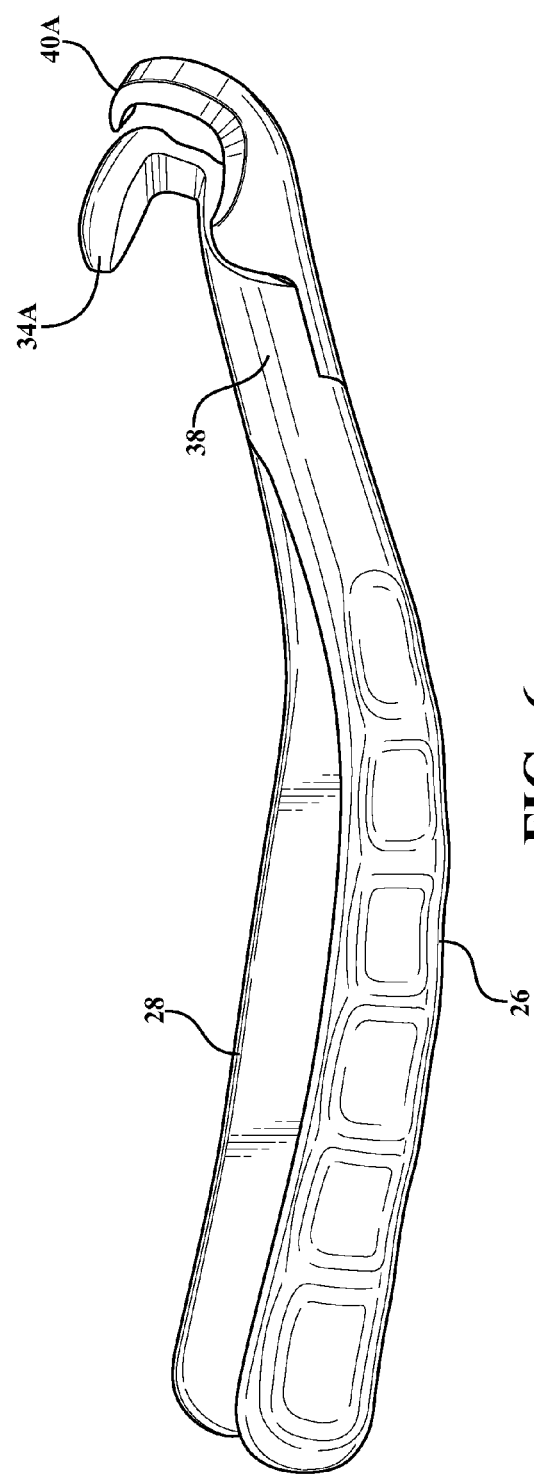
FIG. 5
FIG. 6

FORCEPS FOR MOLAR EXTRACTION

CROSS-REFERENCE TO RELATED APPLICATIONS

This application claims the benefit of U.S. Provisional Patent Application Ser. No. 61/268,523 filed Jun. 12, 2009, which is incorporated herein by reference. The application is also a continuation-in-part of U.S. Utility patent application Ser. No. 11/095,355 filed Mar. 31, 2005.

BACKGROUND OF THE INVENTION

1. Field of the Invention

The present invention relates to forceps for use in the extraction of molars.

2. Description of the Related Art

Forceps for the extraction of molars are known in the art. During use, the surgeon has to exert a great amount of force and leverage on the forceps to extract the molar. In addition, during this application of force, the forceps can shatter the molar prior to removal of the molar from its socket, which requires excessive work and diligence on the part of the surgeon to remove all fragments of the molar from the socket. Accordingly, it would be advantageous to produce a forceps that overcomes these disadvantages.

SUMMARY OF THE PRESENT INVENTION

The present invention discloses a dental forceps which is uniquely configured in any of lower left, lower right, upper left, and upper right variants for assisting in the removal of rear positioned molars from within a patient's mouth, such removal being accomplished quickly through a rotating motion executed by the forcep. The forcep is further configured to assist in removing damaged or fragmented portions of the molar, such as root tips.

Each variant of forceps includes first and second handles which are pivotally connected. Forward distal ends of the handles terminate, respectively, in a first handle support with an end most extending pad having a three dimensional and rounded surface profile which extends to one side of the handle, as well as a second handle terminating in an angled beak. The pad and beak extend at selected and multi-angular offset relative to proximal end locations of the handles such that, upon setting in position at the desired molar by placing the rounded and width extending pad support upon the gum of the patient between the molar and the cheek, i.e., the outside of the jaw and by concurrently placing the pointed beak on the lingual side of the molar, i.e., on the inside of the jaw, an outward rotating force is then exerted on the handles to roll (or rotate) the pad and beak such that the molar is forcibly extracted, with the handles further rotated about the offset and integrally extending support to assist in extracting the molar.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 1 is a perspective view of a lower left molar extraction forceps for removing a lower left molar;

FIG. 2 is a perspective view of a lower right molar extraction forceps for removing a lower right molar;

FIG. 3 is a perspective view of an upper left molar extraction forceps for removing an upper left molar;

FIG. 4 is a perspective view of an upper right molar extraction forceps for removing an upper right molar;

FIG. 5 is another perspective view of the lower left molar extraction forceps;

FIG. 6 is another perspective view of the lower left molar extraction forceps;

DETAILED DESCRIPTION OF THE INVENTION

Referring to the Figures, wherein like numerals indicate like parts throughout the several views, four embodiments of a molar extraction forceps 20A-D are shown. The first, second, third, and fourth embodiments are used to extract a lower left molar, a lower right molar, an upper left molar, and an upper right molar, respectively.

Figure 10:
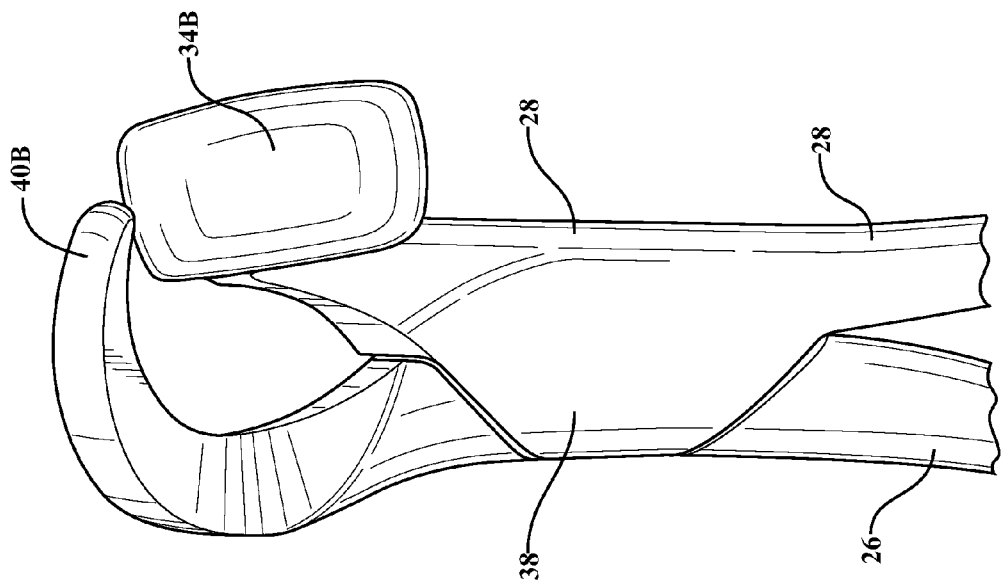
FIG. 10 is a magnified view of a portion of the lower right molar extraction forceps.
Figure 7:
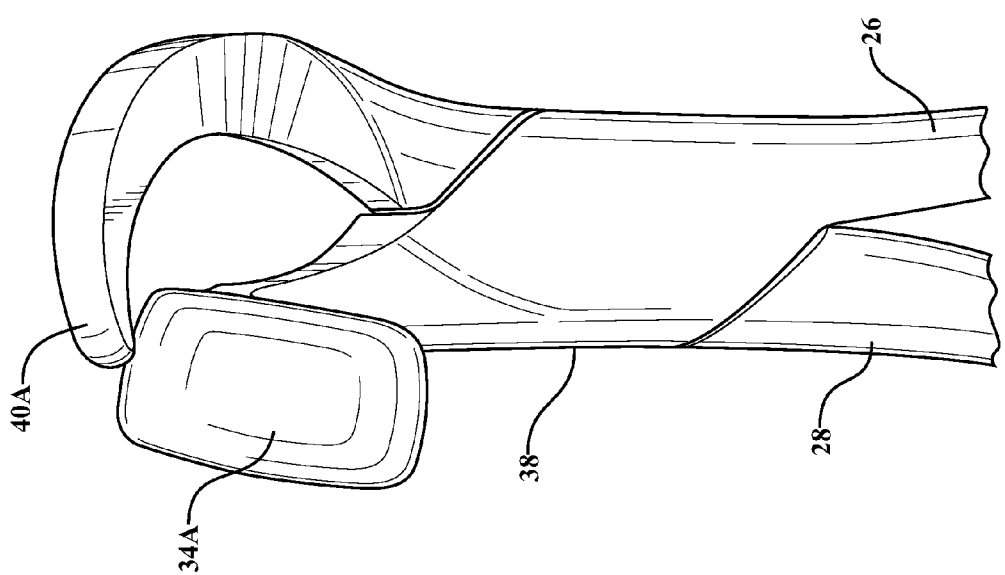
FIG. 7 is a magnified view of a portion of the lower left molar extraction forceps.
Figure 8:
FIG. 8 is another perspective view of the lower right molar extraction forceps.
Figure 9:
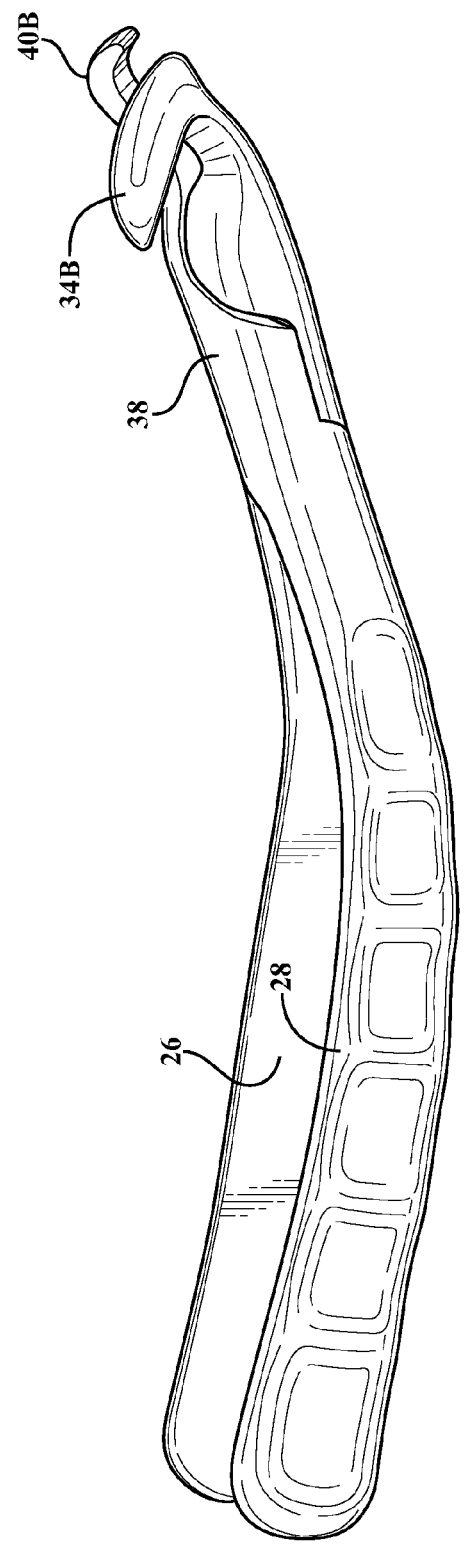
FIG. 9 is another perspective view of the lower right molar extraction forceps.
Figure 11:
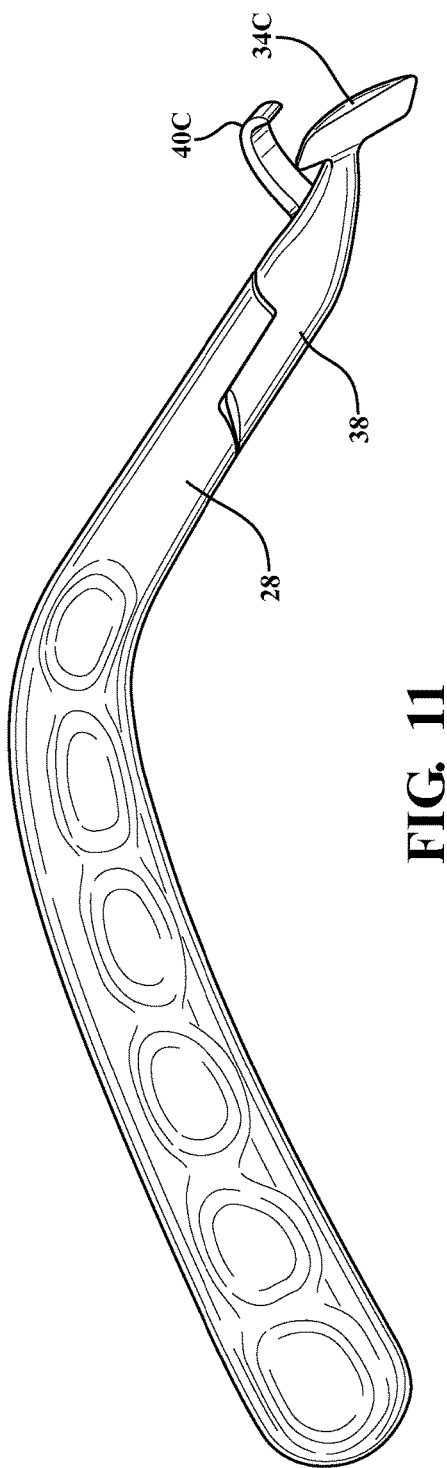
FIG. 11 is another perspective view of the upper left molar extraction forceps.
Figure 12:
FIG. 12 is another perspective view of the upper left molar extraction forceps.
Figure 16:
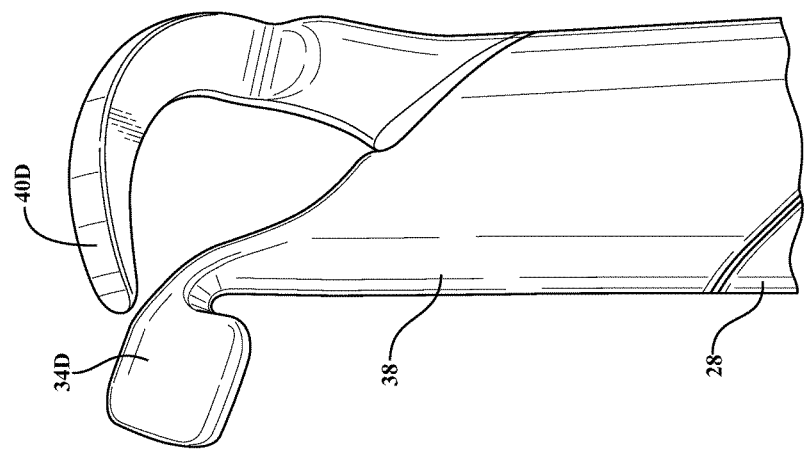
FIG. 16 is a magnified view of a portion of the upper right molar extraction forceps.
Figure 13:
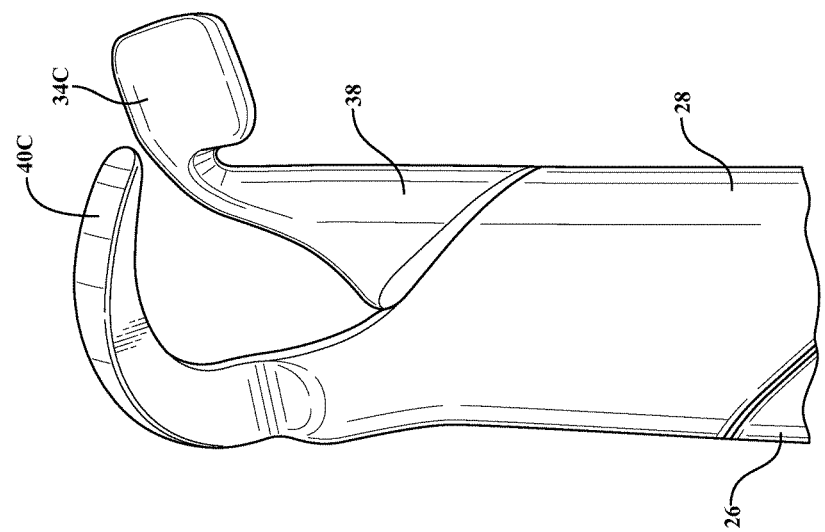
FIG. 13 is a magnified view of a portion of the upper left molar extraction forceps.
Figure 14:
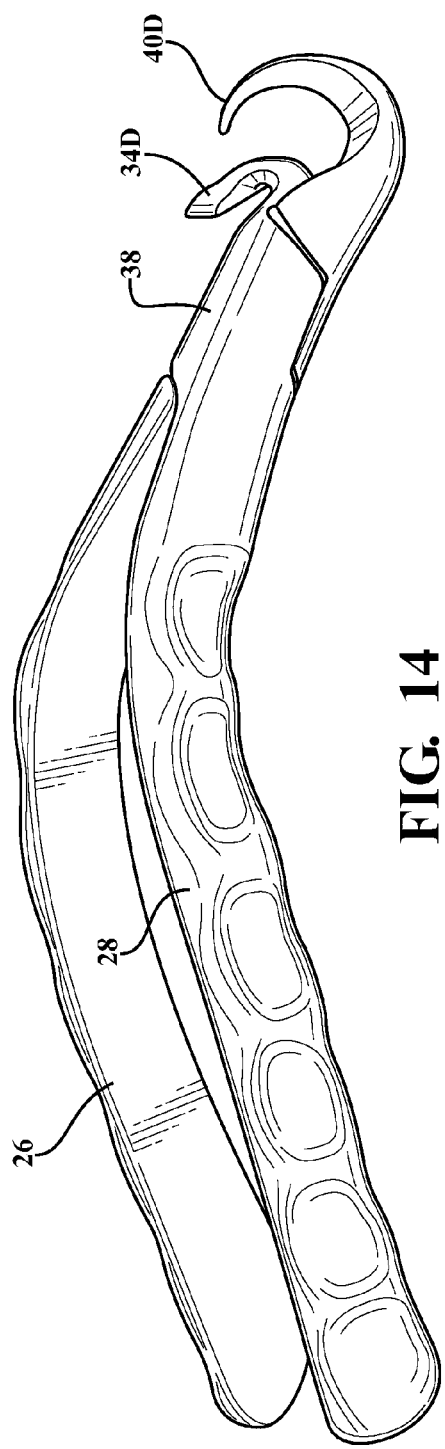
FIG. 14 is another perspective view of the upper right molar extraction forceps.
Figure 15:
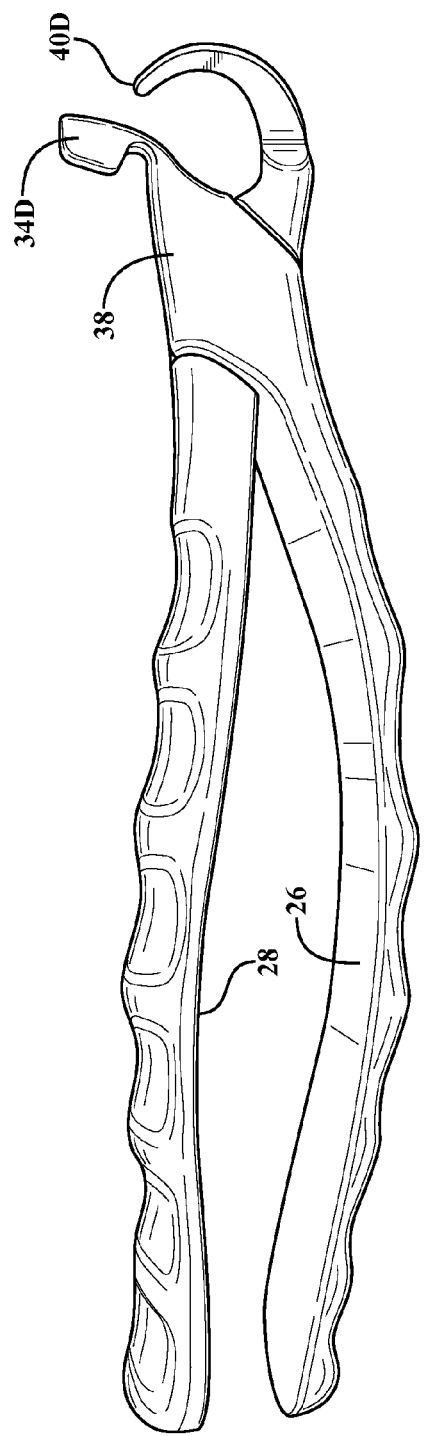
FIG. 15 is another perspective view of the upper right molar extraction forceps.

The first embodiment, shown in FIGS. 1 and 5-7, is a lower left molar extraction forceps 20A for removing the lower left molar. The second embodiment, shown in FIGS. 2 and 8-10, is a lower right molar extraction forceps 20B for removing the lower right molar. The third embodiment, shown in FIGS. 3 and 11-13, is an upper left molar extraction forceps 20C for removing the upper left right molar. The fourth embodiment, shown in FIGS. 4 and 14-16, is an upper right extraction forceps 20D for removing the upper right molar.

Each of the four embodiments include numerous common features and, for simplicity, those features set forth in each of the four embodiments will (unless otherwise specified) be commonly numbered and collectively referred to herein. Likewise, it should be appreciated that the lower left molar extraction forceps 20A and the lower right molar extraction forceps 20B are mirror images of each other, with the upper left molar extraction forceps 20C and the upper right molar extraction forceps 20D likewise being mirror images of each other.

It should also be appreciated that each related variant of forceps 20A-20D is typically used to extract a second or third molar; however can be used to remove any tooth without departing from the nature of the present invention. The use and application of each variant of forceps to remove such as a molar or associated root tip is set forth further below. For purposes of this description, the term molar is further interpreted to include remaining root tip fragments with which the present invention is equally applicable in the removal of.

Referring again to each of the related variants of FIGS. 1-4, the forceps each incorporate a tool constructed of a suitable and durable material, such as a high grade sanitary or like medical grade steel exhibiting the necessary properties of strength and durability and, as commonly denoted in each of the variants of FIGS. 1-4, includes a proximal (rear handle) end 22 and a distal (beak) end 24. Each of the four related variants of forceps 20A-20D further repetitively illustrates a first member (handle) 26 and a second member (handle) 28 each extending from the proximal end 22 to the distal end 24. The first 26 and second 28 members are appropriately configured, such as in generally elongate extending fashion, with distal proximate overlapping locations and such that they are coupled to each other at a pivotal connection (such as by a pin) along a pivotal axis P, as further best referenced in the selected variants of FIGS. 1 (lower left) and 4 (upper right).

Each of the handle shaped portions corresponding to the first and second members 26 and 28 further exhibit any desired surface profile which can include, but is not limited to, a scalloped or contoured portions 30 and 32 and which, in combination with the overall elongated but usually non-linear configuration of the handles, facilitates gripping and manipulation by the dentist or oral surgeon. Each of the elongate handles/members 30 and 32 is further bent such that a portion thereof extends along a first linear axis A (see selected variants of FIGS. 2 and 4), with succeeding portions extending along a second intermediate axis B. As further shown, the first axis A and second axis B extend at an angle X relative to each other.

The first member 26 exhibits an integrally formed support 38 at a location forward of its hinged pivot point and approximate the distal end 24, whereas the second member 28 terminates in a pointed and multi-axial arcuate beak 40 extending in generally spaced apart and opposing fashion relative to the first handle support 38. The support 38 terminates at an end most three dimensional arcuate extending pad 34, which further exhibits an arcuate (or rounded/non-linear) surface profile and which extends laterally to one side of the handle 26 and integral support 38. By design, the pad 34 is intended to be complementary in configuration to the gum of a patient when inserted and manipulated by the user.

The shaping of the pad 34 is further specifically illustrated at 34A, 34B, 34C and 34D in each of the enlarged distal end views of FIGS. 7, 10, 13 and 16, respectively associated with the four related variants and, in combination with the corresponding arrangement of the multi-axial arcuate profile (or hook configuration) exhibited by the associated pointed beaks 40A-40D, are collectively configured to permit the distal end of the forceps to be inserted into the patients mouth without undue discomfort to the patient and further given the multi dimensional and ergonomic mating profile of the distal extending pad 34 and beak 40. The forceps is then manipulated by the user in order that the non-liner/non-planar and arcuate gum line extending support surface of the pad 34, in cooperation with the opposite side arrayed beak 40, are able to properly locate and optimally engage such as rear upper or lower bridge located molars.

This configuration is best depicted in selected variants FIGS. 2 and 4 with the integrally formed support 38 extends from the handle 30 along an axis C that extends at an angle Y relative to axis A, a further axis C1 extending through a greatest width dimension of the pad 34 extending at a further angle Y1 relative to the intermediate support 38 and, by extension, the associated handle 26. Correspondingly, the pointed beak 40 extends from the handle 32 in a multi-directional arcuate fashion such as along an axis D that extends at an angle Z relative to axis A.

In use, the forceps 20 are set in position at the desired molar (not shown) by placing the rounded and width extending pad support 34 upon the gum of the patient between the molar and the cheek, i.e., the outside of the jaw and by concurrently placing the pointed beak 40 on the lingual side of the molar, i.e., on the inside of the jaw. An outward rotating force is then exerted on the handles 26 and 28 to roll (or rotate) the pad 34 and beak 40 such that the molar is forcibly extracted. The handles are further rotated about the offset and integrally extending support 38 to assist in extracting the molar.

The configuration of the forceps 20, e.g., angles X, Y, Y1, and Z, advantageously provides a mechanical advantage to extract the molar in one piece by moving the forceps 20 in a simple rotational movement about the support 38. In addition to the rotational movement about the support 38, the forceps 20 can also be slightly twisted to aid in removal of the molar. Notably, and once the forceps 20 are set in position on the molar, the handles are not squeezed together to tighten the forceps 20 on the molar but rather are rolled to rotate (or in some instances to rock back and forth) the molar. In particular, it is desirous not to squeeze together the handles in order to avoid pinching gum/bone between the molar and the pad 30, as such pinching could limit or prevent the molar from rocking back and forth.

As is shown in the various figures, the support 38 and the pointed jaw 40 extend in a generally offset angular direction than the first handle 26 and second handle 28. That said, it is also appreciated that the support 38 and the pointed jaw 40 can extend in any direction relative to the handles within the scope of the invention.

By design, the selected angles X, Y, and Z incorporated into the design of the forceps are of a magnitude to provide a mechanical advantage when extracting the molar and to properly fit in the mouth of a patient. As is also shown, the magnitude of the angles X, Y, and Z of the lower molar extraction forceps 20A, 20B can be different than the magnitude of the angles X, Y, and Z of the upper molar extraction forceps 20C, 20D. This difference in magnitude can accommodate for different angles and locations of the upper and lower molars. It should also be appreciated that the angles X, Y, and Z can have a magnitude different than that shown in the various figures without departing from the nature of the present invention.

The invention has been described in an illustrative manner, and it is to be understood that the terminology which has been used is intended to be in the nature of words of description rather than of limitation. Obviously, many modifications and variations of the present invention are possible in light of the above teachings, and the invention may be practiced otherwise than as specifically described.

Having described my invention, other and additional preferred embodiments are envisioned and without departing from the scope of the appended claims.

I claim:

1. A dental forceps for dislodging of teeth, comprising:
   first and second handles which are pivotally connected and extend along a first linear axis;
   said first handle exhibiting an angled support at a distal end thereof extending in a second linear axis at angle relative to the first linear axis, a width extending pad at an end location of said angled support, said pad exhibiting a rectangular profile with a gum support surface, a centerline extending through a largest width dimension of said pad extending at a further angle relative to each of the first and second linear axes of said first handle; and said second handle exhibiting a beak extending outwardly from a distal end thereof and having an arcuate portion, said beak extending in a curved fashion relative to each of the first and second linear axes and terminating at a narrowed edge opposing and overlaying an intermediate location of said pad support surface when said handles are in a closed position;

said pad adapted to being placed on one side of a tooth and, upon concurrently placing said terminating edge of said beak against an opposite side of the tooth, a rotating force exerted on said handles results in said pad acting as a fulcrum point around which said beak and terminating edge will move to forcibly dislodge the tooth.

2. The dental forceps as described in claim 1, said forceps being constructed of a medical grade steel.

3. The dental forceps as described in claim 1, each of said first and second handles having a generally elongated profile and further comprising a plurality of enhanced gripping portions.

4. The dental forceps as described in claim 1, said forceps being configured for removal of one of lower left, lower right, upper left and upper right located molars.

5. The dental forceps as described in claim 1, said first and second handles further comprising overlapping locations at a pivotal connection.

* * * * *